(12) United States Patent
Janssen

(10) Patent No.: US 10,293,185 B2
(45) Date of Patent: May 21, 2019

(54) IRRADIATION OF MOVING TARGET USING PARTICLE THERAPY SYSTEM

(71) Applicant: Varian Medical Systems, Inc., Palo Alto, CA (US)

(72) Inventor: James R. Janssen, Santa Cruz, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 15/474,856

(22) Filed: Mar. 30, 2017

(65) Prior Publication Data

US 2018/0280728 A1    Oct. 4, 2018

(51) Int. Cl.
*A61N 5/10*    (2006.01)

(52) U.S. Cl.
CPC ......... *A61N 5/1049* (2013.01); *A61N 5/1037* (2013.01); *A61N 5/1071* (2013.01); *A61N 5/1077* (2013.01); *A61N 2005/1051* (2013.01); *A61N 2005/1072* (2013.01); *A61N 2005/1087* (2013.01)

(58) Field of Classification Search
CPC .. A61N 5/1049; A61N 5/1037; A61N 5/1077; A61N 5/1071; A61N 2005/1051; A61N 2005/1072; A61N 2005/1087

USPC ................. 250/492.1, 492.2, 492.3
See application file for complete search history.

(56) References Cited

U.S. PATENT DOCUMENTS

| | | | |
|---|---|---|---|
| 2011/0309255 A1* | 12/2011 | Bert | A61N 5/1048 250/363.03 |
| 2014/0288349 A1* | 9/2014 | Seeber | A61N 5/1048 600/1 |
| 2015/0094517 A1* | 4/2015 | Prieels | A61N 5/1048 600/1 |

* cited by examiner

*Primary Examiner* — Nicole M Ippolito
*Assistant Examiner* — Hanway Chang (57) ABSTRACT

In an irradiation method, an irradiation plan for irradiating a target volume in phases of motion is provided to a particle therapy system. The particle therapy system comprises a beam delivery device operable to scan a pencil beam of particles over the target volume. The irradiation plan comprises a first field for irradiating the target volume in a first phase of motion and a second field for irradiating the target volume in a second phase of motion. Motion of a tracking device or change of other physical measurement value is monitored and signals continuously indicating the current position of the tracking device or measurement value are provided to the particle therapy system. A pencil beam of particles is applied to the target volume according to the irradiation plan and signals from the tracking system continuously indicating current positions of the target volume. Dosage delivered to the target volume is monitored.

21 Claims, 4 Drawing Sheets

FIG. 7

IRRADIATION OF MOVING TARGET USING PARTICLE THERAPY SYSTEM

TECHNICAL FIELD

Embodiments of this disclosure relate generally to radiation systems and methods. In particular, various embodiments of particle therapy systems, particle irradiation methods, and methods of generating irradiation plans are described.

BACKGROUND

Particle therapy systems for treatment of patients are known. In particle therapy, charged particles such as protons or heavy ions are used to irradiate a target volume such as tumor. One unique feature of particle therapy is that charged particles release most of their energy around the area where they stop because of the "Bragg peak" effect. Therefore, by controlling the energy of charged particles, healthy tissue distal to the source of charged particles receives substantially no radiation and healthy tissue proximal to the source receives significantly reduced amount of radiation. Furthermore, by choosing the energy of charged particles for irradiating different "layers" or "depths" of the target volume, radiation dose distribution can be tailored to the shape of the target in all three dimensions.

Figure 1:
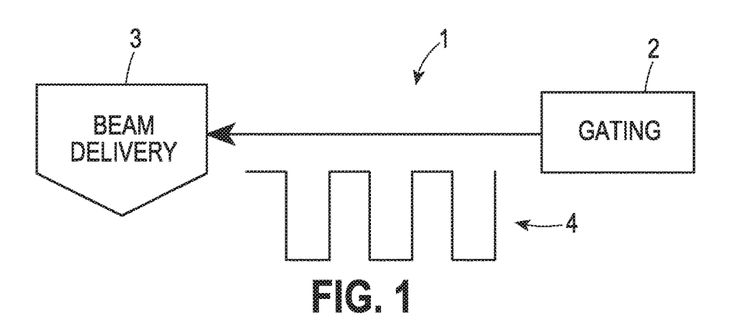
FIG. 1 illustrates a conventional particle therapy system including a gating system providing on/off signals to a beam delivery system.

Movement of a patient undergoing particle therapy presents a challenge, including the accuracy with which the target will be irradiated and sparing the healthy tissue. Normal physiological movement such as respiration or cardiac cycles can cause positional changes of the target volume during treatment. To irradiate a target that is not stationary, "gating" is normally utilized to block the radiation beam whenever the target is out of position. In a gating approach, instruments are utilized to measure the physiological state and/or movement of the patient. These instruments can produce a signal indicative of the movement of the target e.g. during the respiratory cycle. The radiation beam can be gated based upon certain threshold amplitude levels of the measured signal such that the radiation beam is blocked or disengaged during particular time points in the signal that corresponds to excessive movement of the target. FIG. 1 illustrates a conventional particle system 1 where a gating system 2 is coupled to a beam delivery system 3. Gating signals 4, which are synchronized to the movement of a target, are provided to the beam delivery system 3 for turning on and off the radiation beam.

While the conventional gating approach can reduce the amount of healthy tissue irradiated, it typically requires that the beam be turned off for a large period of time during the treatment, leading to increased treatment time and decreased patient throughput. The gating approach also represents inefficient usage of the facility's most valuable resource, beam time.

SUMMARY

Embodiments of a particle therapy system and an irradiation method are provided in the disclosure to allow continuous irradiation during some or all of the time that the particle beam would be interrupted by gating in conventional gated irradiation. According to the disclosure, in addition to a "base field" corresponding to a normal "gated" plan, additional "displaced fields" may be defined to represent target's positions in phases of motion when the beam would be blocked during a gated irradiation. A signal may be provided to the control of a beam delivery system that continuously indicates the position of an anatomical tracking marker, which serves as an analog of the target position. With these enhancements, the particle therapy system can continue irradiation during some or all of the time that the beam would normally be interrupted by gating. Instead of blocking the beam when the target moves, the beam delivery system may utilize a displaced field that corresponds to the current position of the tracking marker to continue irradiation. In cases where the target motion is only transverse to the beam (X and Y dimensions) as seen by the beam delivery device, displaced fields can be defined that always allow continuous irradiation. In cases that the target also exhibits motion along the direction of the beam (Z dimension), the situation may be more complex, but it is still often possible to irradiate during some of time that the beam would be blocked in a conventional gated plan.

Therefore, according to embodiments of this disclosure, instead of using a gating system to transmit a simple on/off signal to the beam delivery device, a position-tracking system is utilized to continually transmit the current marker position to the beam delivery device, using an analog signal or an equivalent digital stream.

Treatment planning according to embodiments of this disclosure may start as usual for a gated irradiation. This field may be termed as the "base field." In addition to the base field, one or more "displaced fields" may be defined. Each displaced field represents the target volume at a particular position of the anatomical tracking marker where the beam would be blocked in a normal gated plan. Each target spot in a displaced field represents the displaced position of the target spot in the base field. Therefore the total dose for each spot may be accumulated in the base field data, whether the base field or a displaced field is actually used to specify the beam position. A standard gated irradiation is a special case of the disclosed scheme with zero displaced fields. Because the beam energy of a particle therapy system cannot be changed quickly, the displaced fields utilize the same set of energy levels as the base field.

The radiation system may be programmed or configured to perform irradiation using the new scheme. Once the irradiation plan is loaded, the beam delivery device receives the base field and all associated displaced fields in the plan. All of the fields may be converted to the device internal spotlist values. Irradiation of a given spot will stop in the case when its dose target is hit, or whenever the tracking position has moved out of the acceptable range for the current spot. Since the tracking position moves continuously, the beam delivery device can pre-compute what to do in the case that the tracking position goes out of range to the next larger or smaller value.

Accordingly, provided is a particle therapy system comprising a beam delivery device operable to scan a pencil beam over a target volume, a control operable to control the beam delivery device, and a tracking system configured to monitor measured values corresponding to motions of the target volume and transmit signals continuously indicating current measured tracking values to the control, thereby allowing the control to control the beam delivery device to continuously scan the target volume according to an irradiation plan while the target volume is in phases of motion. The tracking system may transmit an analog signal or an equivalent digital stream continuously corresponding to current positions of the target volume in phases of motion to the control. In an exemplary embodiment, the tracking system comprises a marker indicative of a current position situated to maintain a fixed relationship with the current position of the target volume in all phases of motion and an optical camera monitoring movement of the marker.

In one aspect, an irradiation method is provided. According to the irradiation method, an irradiation plan is provided to a particle therapy system for irradiating a target volume in phases of motion. The particle therapy system comprises a beam delivery device operable to scan a pencil beam of particles over the target volume. The irradiation plan comprises a first field for irradiating the target volume in a first phase of motion and a second field for irradiating the target volume in a second phase of motion. Motion of the marker or change of other physical measurement value is monitored and signals continuously indicating current position or measurement value are provided to the particle therapy system. A pencil beam of particles is applied to the target volume according to the irradiation plan and based on the signals from the tracking system. The particle therapy system continuously determines current positions of the target volume. Dosage delivered to the target volume is monitored.

The target volume may comprise a first target spot and a second target spot. The first field of the irradiation plan may include data for irradiating the first and second target spots of the target volume in the first phase of motion. The second field of the irradiation plan may include data for irradiating at least the second target spot of the target volume in the second phase of motion. In applying the pencil beam to the first target spot of the target volume in the first phase of motion, if a prescribed dosage to the first target spot has been reached and if the target volume is still in the first phase of motion, then the pencil beam stops irradiating the first target spot and starts to irradiate the second target spot according to data of the first field. If a prescribed dosage to the first target spot has not been reached and the target volume is indicated to be in the second phase of motion, and the second field includes data for irradiating the first target spot, then the pencil beam continues to irradiate the first target spot according to data of the second field until a prescribed dosage to the first target spot has been reached. If the second field does not include data for irradiating the first target spot, then the pencil beam irradiates the second target spot according to data of the second field.

In embodiments of the disclosure, the target volume may consist of one or more target spots, and measured values corresponding to motion of each of the one or more target spots may be monitored and signals continuously indicating current measured tracking values may be provided to the particle therapy system for controlling beam delivery according to an irradiation plan.

In another aspect, a method of generating an irradiation plan for irradiating a moving target volume with a pencil beam of particles is provided. According to the method, phases of motion of a target volume that exhibits motion in a plane generally transverse to the direction of a pencil beam are determined. A first field for scanning the target volume in a first phase of motion is defined. A second field for scanning the target volume in a second phase of motion is defined. An irradiation plan for continuously irradiating the target volume moving from the first phase to the second phase is generated, wherein while the target volume is in the first phase of motion the first field is used for the pencil beam to scan the target volume and wherein while the target volume is in the second phase of motion the second field is used for the pencil beam to scan the target volume.

The target volume may comprise one or more target spots. In defining the first field, data on positions of each of the one or more target spots may be provided. In defining the second field, data on positions of each of the one or more target spots may be provided. In some embodiments, at least one of the one or more target spots may be continuously irradiated with the pencil beam while the target volume moves from the first phase to the second phase of motion to reach a prescribed dosage, wherein in the first phase of motion, the at least one of the one or more target spots is irradiated according to the first field and in the second phase of motion, the at least one of the one or more target spots is irradiated according to the second field.

In a further aspect, a method of generating an irradiation plan for a moving target volume with pencil beams of particles is provided. According to the method, phases of motion of a target volume that exhibits motion in a dimension generally parallel to the direction of a pencil beam of particles are determined. The target volume may comprise at least a first layer and a second layer along the direction of the pencil beam. A first field for irradiating the target volume in a first phase of motion is defined wherein at least a first pencil beam having a first energy level scans the first layer of the target volume and a second pencil beam having a second energy level scans the second layer of the target volume. A second field for irradiating the target volume in a second phase of motion is defined wherein the first pencil beam having the first energy level scans the second layer of the target volume or the second pencil beam having the second energy level scans the first layer of the target volume. An irradiation plan for continuously irradiating the target volume when moving from the first phase to the second phase is generated, wherein the first pencil beam having the first energy level scans the target volume in both the first and the second phases of motion, or the second pencil beam having the second energy level scans the target volume in both the first and the second phases of motions. In defining the first field, data on locations of the first and second layers of the target volume may be provided. In defining the second field data on locations of the first and second layers of the target volume may be provided.

According to embodiments of the irradiation plan, the first pencil beam having the first energy level continuously irradiates the target volume when the target volume moves from the first phase to the second phase, wherein the first pencil beam having the first energy level irradiates the first layer of the target volume according to the first field when the target volume is in the first phase and irradiates the second layer of the target volume according to the second field when the target volume is in the second phase. Alternatively, the second pencil beam having the second energy level continuously irradiates the target volume while moving from the first phase to the second phase of motions, wherein the second pencil beam having the second energy irradiates the second layer of the target volume according to the first field when the target volume is in the first phase and irradiates the first layer of the target volume according to the second field when the target volume is in the second phase.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Various embodiments of radiation systems are described. It is to be understood that the disclosure is not limited to the particular embodiments described. An aspect described in conjunction with a particular embodiment is not necessarily limited to that embodiment and can be practiced in any other embodiments.

Various embodiments are described with reference to the figures. It should be noted that some figures are not necessarily drawn to scale. The figures are only intended to facilitate the description of specific embodiments, and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components or process steps may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. Further, the term "first" or "second" etc. may be used to distinguish one element from another in describing various similar elements. It should be noted the terms "first" and "second" as used herein include references to two or more than two. Further, the use of the term "first" or "second" should not be construed as in any particular order unless the context clearly dictates otherwise.

As used herein, the term "particle beam" or its grammatical equivalents refers to a beam of charged particles such as protons or heavy ions such as ions of helium, carbon, neon, argon, or other charged elemental particles.

As used herein, the term "a phase of motion of a target" or its grammatical equivalents refers to a given time or phase in a motion cycle of a target caused by patient's physiological movement such as breathing or cardiac movement. As used herein, "a first phase of motion" distinguishes from "a second phase of motion" in that a particle beam for irradiating a moving target in the first phase of motion would have been blocked or disengaged when the target moves into the second phase of motion, or vice versa, in a conventional gated particle therapy. A target may exhibit motions in dimensions (X and Y) generally traverse to the direction of the particle beams. A target volume may also exhibit motions in the dimension (Z) generally parallel to the direction of the particle beams. In charged particle therapy, the energy of a particle beam for irradiating a layer or depth of a target generally does not strongly depend on the target's proximity to the beam source, but rather more on the anatomical structures between the target and the surface of the patient, and these structures tend to move along with the target. Therefore, many cases of target motions can be considered to have X and Y motions as "seen" by the beam source and hence can be irradiated according to methods of this disclosure without interrupting the beam for gating.

As used herein, the term "field" refers to a plan prepared for irradiating a target in a phase of motion. A field may include data on the location of the target or locations of target spots consisting of the target in a coordinate system, dosage to be applied to the target or target spots, and values describing the range of the position tracking system's measurement for which the field is valid. By way of example, a first field includes data for irradiating the target in a first phase of motion cycle and a second field includes data for irradiating the target in a second phase of motion cycle. The term "base field" may sometimes be used to refer to a field for irradiating the target in a phase of a motion cycle that the target can best be irradiated. The determination of the base field may be based on numerous factors including the expected reproducibility of the target position relative to marker position, the position of surrounding tissues in the various fields, and the rate of position change. The term "displaced fields" may be used to refer to fields for irradiating the target in phases of motion other than the phase selected for the base field, during which particle beams would be blocked or disengaged in normal gating schemes.

Figure 2:
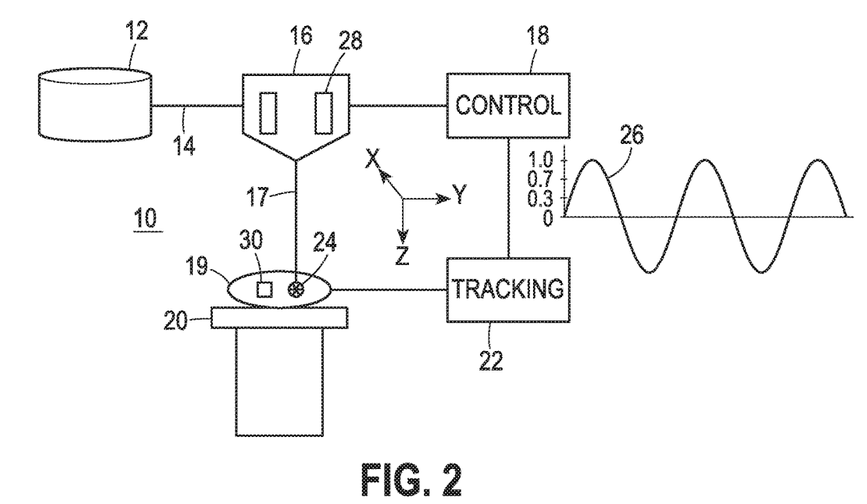
FIG. 2 illustrates an exemplary particle therapy system including a tracking system according to embodiments of this disclosure.

FIG. 2 illustrates an exemplary particle therapy system 10 according to embodiments of this disclosure. As shown, the exemplary particle therapy system 10 includes an accelerator 12, a beam transport line 14, a beam delivery device 16, and a control 18. A subject 19, such as a patient to be irradiated, is positioned on a support 20. A tracking system 22 measures the position of marker 30 or the value of other externally-measurable physical characteristic, and transmits signals 26 continuously indicating the measured values to the control 18. The control 18 controls the operation of the beam delivery device 16 according to an irradiation plan and based on the signals 26 received from the tracking system 22.

The accelerator 12 may include a source of charged particles such as protons or heavy ions such as ions of helium, carbon, neon, argon, or other charged elemental particles. The accelerator 12 may include a cyclotron, synchrotron, linear accelerator, or any other accelerators configured to accelerate charged particles. The energy of the charged particles may be greater than 20, 50, 70, 100, 250 or 500 MeV depending on specific applications.

The beam transport line 14 transports a beam of charged particles from the accelerator 12 to the beam delivery device 16 typically located in a treatment room different from that of the accelerator 12. While a single beam delivery device 16 is shown, the particle therapy system 10 may include two or more beam delivery devices located in different treatment rooms and thus two or more beam transport lines used to transport charged particles from the accelerator 12 to two or more treatment rooms. Bending magnets (not shown) may be used to guide a particle beam from the accelerator 12 to the beam delivery device 16. The beam transport line 14 may include energy modification components (not shown) such as energy degraders for modifying the energy of particles extracted from the accelerator and slits for adjusting the intensity of particles from the accelerator.

The beam delivery device 16 operates to deliver a pencil beam 17 of particles to the target volume 24 in the patient 19. The beam delivery device 16 may include various components or devices for modulating and monitoring the particle beam. Depending on applications, the beam delivery device 16 may include energy modifiers, scanning magnets, beam monitors, collimators, compensators, or other components configured to modulate the particle beam.

In some embodiment, the beam delivery device 16 may include scanning magnets 28 configured to scan a pencil beam 17 in a plane generally transverse the direction of the pencil beam. The scanning magnets 28 may cause a pencil beam 17 to continuously move along predetermined scanlines over a slice or layer of a target volume 24. The power supplied to the scanning magnets 28 may be controlled to vary the strength of the electromagnetic field generated. The energy of the particles of the pencil beam 17 may be selected such that the Bragg peaks of the scan are deposited on the predetermined slice or layer of the target volume 24. By changing the energy of the particle beam, other slices of the target volume 24 can also be irradiated, layer by layer. In some embodiments, the beam delivery device 16 may rotate about an axis e.g. a horizontal axis passing through an isocenter in order to deliver a particle beam to the target volume 24 from various angles. Alternatively, the beam delivery device 16 may deliver a particle beam from a fixed direction.

The tracking system 22 may monitor a physical signal which, e.g. like the measured position of marker 30, varies in direct correspondence with the motion or position of the target volume 24 in the patient 19. The tracking system 22 may transmit signals 26 continuously indicating the value measured by the tracking system 22 to the control 18, which may utilize the field data to determine the corresponding position of the target volume 24. Various suitable tracking systems may be used. By way of example, the tracking system 22 may include an imaging device which can continuously track one or more motion surrogates directly correlated to the motion and/or position of the target volume 24. These surrogates may include, for example, respiratory markers or ECG signals. Other systems and methods for tracking a target volume may include, but are not limited to, implanted sensors, real-time imaging devices, or any other device suitable to monitor organ motion and/or the respiratory or cardiac cycle(s) of a patient. The tracking system 22 may further include a computer to analyze the monitored motion and transmit the analyzed motion characteristics to the control 18. For example, signals from the markers or surrogates may be processed using techniques known in the art to correlate the external motion of markers or surrogates with the motion or position of the target volume in real time. In some embodiments, an analog signal or an equivalent digital stream continuously indicating the value measured by the tracking system 22, as indicated by 26, may be produced and transmitted to the control 18.

In a specific embodiment, the tracking system 22 may include an optical or video image camera (not shown) placed e.g. on the ceiling, wall, or other support structure and one or more markers 30 located on the patient 19 in the area to be detected for movement. The tracking system 22 may also include one or more illumination sources (not shown) such as infrared light sources, which may be located at the camera, to project light at the markers 30 on the patient 19. The one or more markers 30 may reflect light from the illumination sources and the camera captures and detects the reflected light from the one or more markers 30. Monitoring of a target volume 24 may include measuring a frequency and duration of each phase or cycle of a periodic motion exhibited by the target volume (e.g., displacement from a resting or default position) and the timing (e.g., duration) of transitions between phases. Monitoring of a target volume 24 may also include measuring the direction and the peak displacement from the resting or default position.

In an alternative embodiment, the tracking system 22 may include a tracking device configured to measure the amount of air being inhaled and exhaled by the patient, to ascertain the volume of air currently in the patient's lungs and thereby determine their current breathing phase. Exemplary devices include but are not limited to spirometers or spirometric motion management systems, which can pair a patient's inspiration rate and lung volume measurement.

The control 18 controls the operation of the beam delivery device 16. The control 18 may store irradiation plans associated with the patient 19. The control 18 may receive and use the signal 26 continuously indicating current monitored measurements in executing the irradiation plans. By way of example, the control 18 may control the power supplied to the scanning magnets 28 to vary the magnetic field strength and the timing to adjust the direction and sequence of the particle beam 17. The control 18 may include a general-purpose computer or a special-purpose computer with software and hardware adapted for applications of particle therapy. The control 18 can be implemented as part of the mechanical and electrical structure of the beam deliver device. Alternatively, the control can be an external apparatus that is connected to the electronics of the beam delivery device.

Figure 3:
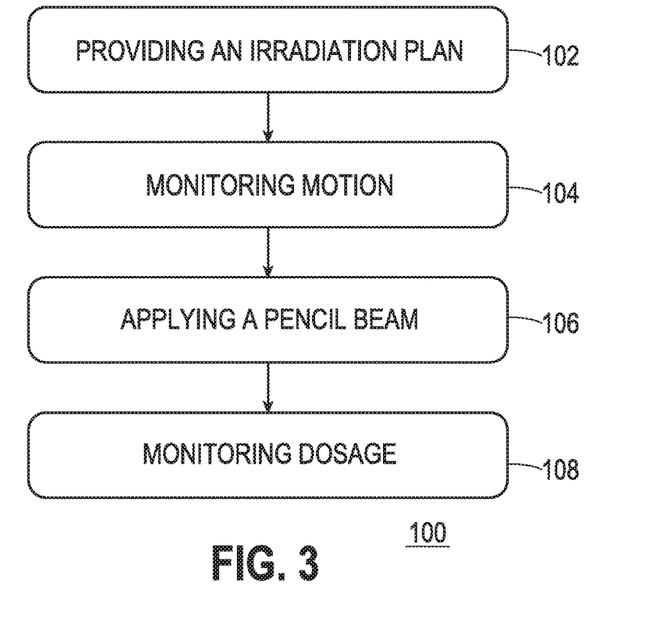
FIG. 3 is a flowchart showing an irradiation method according to embodiments of this disclosure.

FIG. 3 is a flowchart illustrating an irradiation method 100 according to embodiments of this disclosure. The irradiation method 100 may be implemented in the radiation system 10 described above in connection with FIG. 2 or similar systems. The method 100 may start by providing an irradiation plan for irradiating a moving target volume to a particle therapy system (step 102). The irradiation plan may be generated according to embodiments of the present disclosure, as will be described in greater detail below. In general, the irradiation plan may include at least a first field for irradiating the target volume in a first phase of motion and a second field for irradiating the target volume in a second phase of motion.

The first and second fields may be prepared during a treatment planning session. By way of example, during a treatment planning session, a series of x-ray images covering a full motion cycle of the patient, e.g. a respiration or cardiac cycle, may be acquired using computed tomography (CT). Each of the CT images may correlate to the data on a specific phase of motion of the patient. A group of CT images of the same or similar phase can be obtained and reconstructed to provide a three-dimensional image of the patient structure at a specific phase of motion of the patient. By way of example, a first field may be prepared using CT images correlating to the data on the position marker range value from 0.00 to 0.3 (e.g. a base field). A second field may be prepared using CT images correlating to the data on a position marker range value from 0.3 to 0.7, a third field may be prepared using CT images correlating to the data on the position marker range value from 0.7 to 1.0, and so on. In conventional particle therapy, the particle beam is normally gated or disengaged when the position marker indicates that the target volume is out of the base field, i.e., the position marker range value is out of 0.0-0.3.

In embodiments of the disclosure, the first field may be a field for irradiating the target in the phase of a motion cycle that provides the best opportunity to irradiate the target volume. In a motion cycle of the target volume caused by respiration, for example, the phase between the end of an exhalation and the beginning of an inhalation typically provides the best opportunity for irradiating the target volume, as the target volume is relatively stationary at that point. This field may be referred to as a "base field." A base field may correspond to a "gated plan" in the conventional gating scheme. The fields for irradiating the target volume in other phases of a motion cycle may be referred to as "displaced fields."

The first field may include data about the location of the target volume, the dosage applied to the target volume, and values describing the range of position-tracking system's measurement corresponding to the first field. The second field may include data about the location of the target volume, the dosage applied to the target volume, and the range of position-tracking system's measurement corresponding to the second field. In embodiments of the disclosure, the target volume may consist of a plurality of target spots to be scanned by a pencil beam. As such, the first and second fields may include data about locations of each of the target spots and reference numbers associated with each of the target spots.

Still referring to FIG. 3, during irradiation, motion of the marker or change of other physical measurement value is monitored and signals continuously indicating the current position of the marker or measurement value are transmitted to the particle therapy system (step 104). The monitoring of motion and transmitting of signals can be accomplished by a tracking system 22 shown in FIG. 2 or any other suitable systems described above.

At step 106, a pencil beam is activated and applied to the target volume according to the irradiation plan and the signals provided by the tracking system.

The dosage delivered to a target volume is monitored at step 108. The monitoring of the dosage can be accomplished by a dosage monitoring device (not shown) within the beam delivery device 16. Irradiation or stop of irradiation of a given target spot will depend on the monitoring of dosage to the target spot and tracking position whether the spot has moved out of the acceptable range for the current spot. The following examples illustrate various spot irradiation cases.

Case 1: A target spot completes irradiation because the dose target has been reached. Result: The beam moves to the next spot in the current field and continues irradiating.

Case 2: A target spot is out of range of the current field (base or displaced) and the next field (corresponding to the new tracking position) also contains data for that same spot. Result: The beam delivery device continues irradiating the same spot using the updated field data.

Case 3: A target spot is out of range of the current (base or displaced) field, and the field corresponding to the new tracking position does not contain data for that same spot but does have other unfinished spots in the current energy layer. Result: The beam delivery device continues irradiating the next unfinished spot using the updated field data.

Case 4: A target spot stops being irradiated because the tracking position is out of range of the current (base or displaced) field, and the field corresponding to the new tracking position does not contain any other unfinished spots in the current energy layer. Result: The beam delivery device interrupts irradiation until it can complete the current layer.

Figure 4:
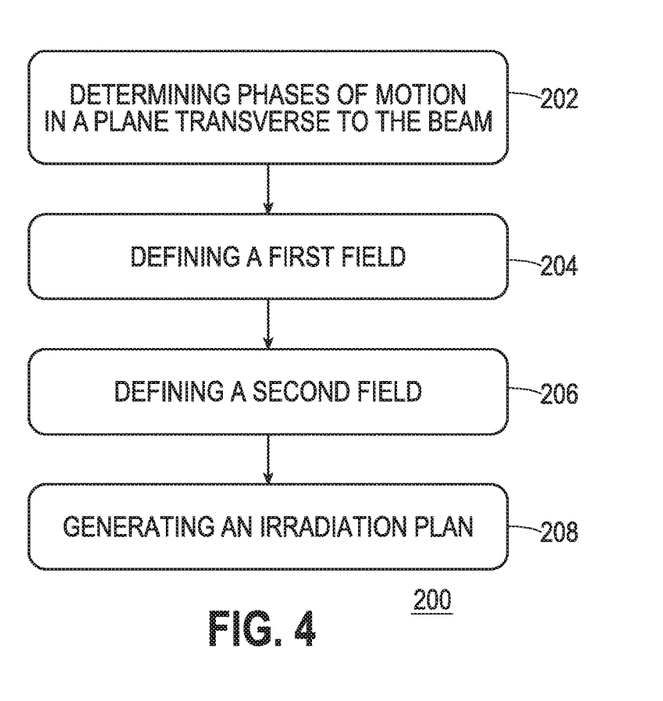
FIG. 4 is a flowchart showing a method for generating an irradiation plan according to embodiments of the disclosure.

FIG. 4 is a flowchart illustrating a method 200 for generating an irradiation plan for irradiating a target volume that exhibits motion in a plane generally transverse to the pencil beam according to embodiments of this disclosure.

The method 200 may start by determining phases of motion of a target volume (step 202). This can be accomplished by a tracking system described above. In particle therapy, the beam energy for irradiating a layer or depth of a target volume generally does not strongly depend on the target's proximity to the beam source, but rather more on the anatomical structures between the target and the surface of the patient, and these structures tend to move along with the target. Therefore, many cases of a target motion can be considered in a plane generally transverse to the pencil beam (X and Y dimensions) as "seen" by the beam source and hence can be planned as such.

At step 204, a first field (e.g. a base field) is defined for scanning the target volume with a pencil beam when the target volume is in a first phase of motion. The first field may include data about the location of the target volume, the dosage applied to the target volume, and values describing the range of position-tracking system's measurement corresponding to the first field. In embodiments of the disclosure, the target volume consists of a plurality of target spots to be scanned by a pencil beam and the first field may include data about locations of each of the target spots and reference numbers associated with each of the target spots.

At step 206, a second field (e.g. a displaced field) is defined for scanning the target volume with the pencil beam when the target volume is in a second phase of motion. The second field may include data about the location of the target volume, the dosage applied to the target volume, and values describing the range of position-tracking system's measurement corresponding to the second field. In embodiments of the disclosure, the target volume consists of a plurality of target spots to be scanned by a pencil beam and the second field may include data about locations of each of the target spots and reference numbers associated with each of the target spots.

The first and second fields may be defined according to the method described above. For example, a series of x-ray images covering a full motion cycle of the patient e.g. the respiration or cardiac cycle may be acquired using computed tomography (CT). Each of the CT images may correlate to data on a specific phase of motion of the patient. A group of CT images of the same or similar phase can be obtained and reconstructed to provide a three-dimensional image of the patient structure at a specific phase of motion of the patient. Data for the first and/or the second fields can be then defined, including locations of the target or target spots, reference numbers associated with each of the target spots, dosage applied to the target spots, and values describing the range of position-tracking system's measurement corresponding to the field.

At step 208, an irradiation plan is generated for continuously irradiating the target volume when moving from the first phase to the second phase. In the irradiation plan, the first field is used for the pencil beam to scan the target volume while the target volume is in the first phase of motion, and the second field is used for the pencil beam to scan the target volume while the target volume is in the second phase of motion.

Figure 5:
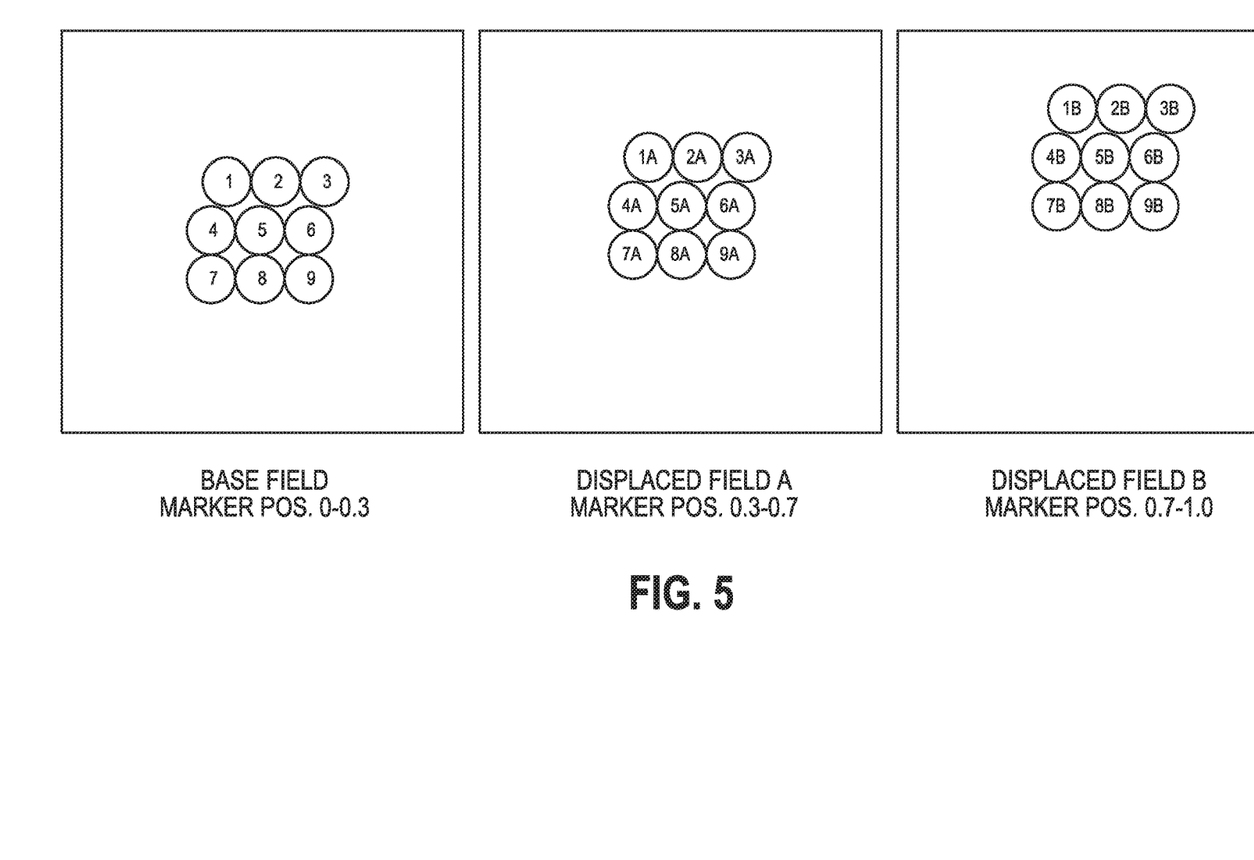
FIG. 5 depicts a base field and two displaced fields further illustrating the method shown in FIG. 4.

FIG. 5 schematically illustrates a first field (base field) and two displaced fields (A, B) defined according to the method described above for irradiating a target that exhibits motion in a plane generally transverse the pencil beam. The left panel of FIG. 5 depicts a base field, which may correspond to a marker position having a range measurement value of e.g. 0.0-0.3. The middle panel of FIG. 5 depicts a displaced field, which may correspond to a marker position having a range measurement value of e.g. 0.3-0.7. The right panel of FIG. 5 depicts another displaced field, which may correspond to a marker position having a range measurement value of e.g. 0.7-1.0. For illustration purpose, the target volume depicted in FIG. 5 is shown to consist of nine (9) target spots. It will be appreciated that the target volume may include more or fewer than nine target spots. Further, more or fewer than two displaced fields may be defined based on applications.

As shown in FIG. 5, irradiation may start when the anatomical marker is in position 0.0. The system may finish with spots 1 and 2, and midway with spot 3 when the marker position reaches 0.3. Before reaching the marker position of 0.3, the system carries out irradiation according to the data defined in the base field (the left panel of FIG. 5).

When the marker position reaches 0.3, the system may continue to irradiate spot 3 but using the data defined in the first displaced field (data associated with reference number 3A in the middle panel of FIG. 5). Irradiation of spots 3A and 4A may complete, and part way through spot 5A before the marker position reaches 0.7.

When the marker position reaches 0.7, the system may continue to irradiate spot 5B, 6B, etc. using the data of the second displaced field (the right panel of FIG. 5).

Figure 6:
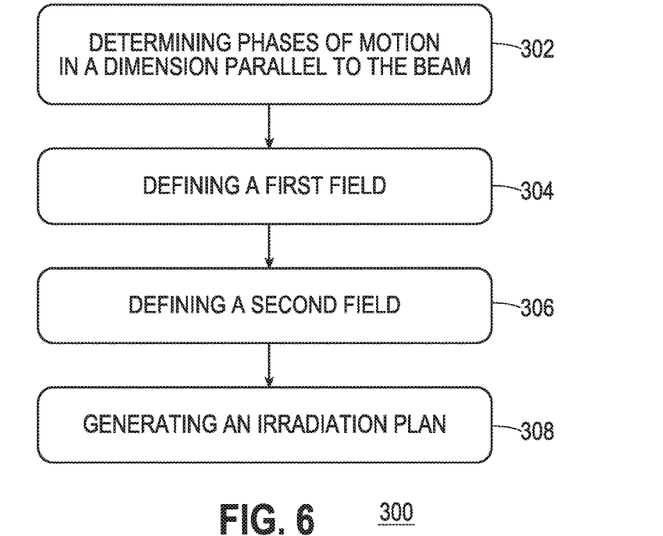
FIG. 6 is a flowchart showing a method for generating an irradiation plan according to alternative embodiments of the disclosure.

FIG. 6 is a flowchart illustrating a method 300 for generating an irradiation plan for irradiating a target volume that exhibits motion in a dimension generally parallel to the direction of pencil beams according to embodiments of this disclosure.

The method 300 may start by determining phases of motion of a target volume that exhibits motion in a dimension generally parallel to the pencil beams of particles (step 302). This can be accomplished by a tracking system described above. The target volume comprises at least a first layer and a second layer to be irradiated by pencil beams of different energy levels.

At step 304, a first field for irradiating the target volume in a first phase of motion is defined, wherein at least a first pencil beam having a first energy level scans the first layer of the target volume and a second pencil beam having a second energy level scans the second layer of the target volume.

At step 306, a second field for irradiating the target volume in a second phase of motion is defined, wherein the first pencil beam having the first energy level scans the second layer of the target volume or the second pencil beam having the second energy level scans the first layer of the target volume.

At step 308, an irradiation plan for continuously irradiating the target volume when moving from the first phase to the second phase is generated. In the irradiation plan, the first pencil beam having the first energy level scans the target volume when in both the first phase and the second phase of motion, or the second pencil beam having the second energy level scans the target volume when in both the first phase and the second phase of motion.

Figure 7:
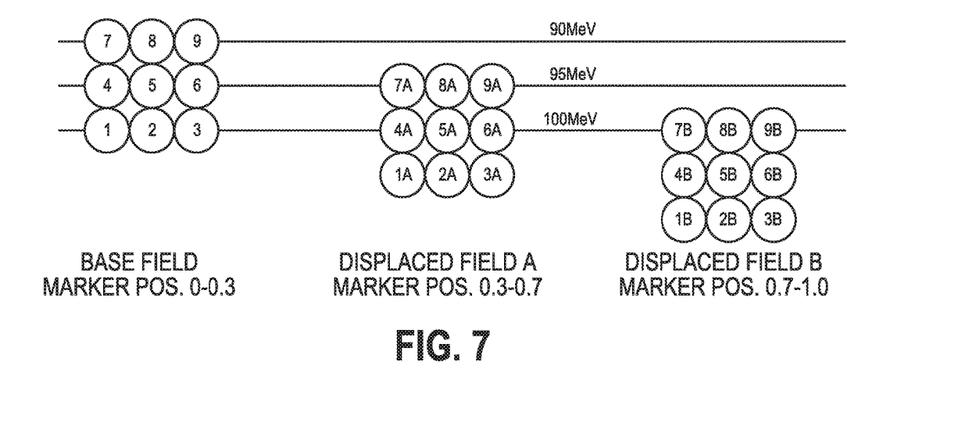
FIG. 7 depicts a base field and two displaced fields further illustrating the method shown in FIG. 6.

FIG. 7 schematically illustrates a base field and two displaced fields (A, B) defined according to the method described above for irradiating a target that exhibits motion in a dimension generally parallel to the direction of the pencil beams. For illustration purpose, the target volume depicted in FIG. 7 is shown to consist of nine (9) target spots. It will be appreciated that the target volume may include more or fewer than nine target spots. Further, it will be appreciated that more or fewer than two displaced fields may be defined based on applications.

The left panel of FIG. 7 depicts a base field, which may correspond to a marker position having a range measurement value of e.g. 0.0-0.3. Target spots 1, 2, and 3 in a first layer are defined to be scanned with a first pencil beam having an energy level of e.g. 100 MeV. Targets spots 4, 5, and 6 in a second layer are defined to be scanned with a second pencil beam having an energy level of e.g. 95 MeV. Targets spots 7, 8, and 9 in a third layer are defined to be scanned with a third pencil beam having an energy level of e.g. 90 MeV.

The middle panel of FIG. 7 depicts a displaced field, which may correspond to a marker position having a range measurement value of e.g. 0.3-0.7. In this displaced field, targets spots 4, 5, and 6 in the second layer are defined to be scanned with the first pencil beam having an energy level of e.g. 100 MeV, and targets spots 7, 8, and 9 in the third layer are defined to be scanned with the second pencil beam having an energy level of e.g. 95 MeV. Because the energy levels are defined as part of the base field, only the displaced field layers that correspond to base field energies will be irradiated. In the example shown in the middle panel of FIG. 7, target spots 1-3 would not be irradiated since they are out of the depth range.

The right panel of FIG. 7 depicts another displaced field, which may correspond to a marker position having a range measurement value of e.g. 0.7-1.0. In this displaced field, targets spots 7, 8, and 9 in the third layer are defined to be scanned with the first pencil beam having an energy level of e.g. 100 MeV. In the example shown in the right panel of FIG. 7, target spots 1-6 would not be irradiated since they are out of the depth range.

FIG. 7 shows that fields may be defined to continuously irradiate a target volume that exhibits motion in Z direction. For example, if irradiation with the first pencil beam having an energy level of 100 MeV commences when the marker position is 0.0, and is midway through spot 3 when the marker position passes 0.3, then irradiation with the first pencil beam may continue with spot 4 and 5 using the data of the displaced field "A" instead of gating the beam. Similarly, if irradiation of target spots 4, 5, and 6 with the first pencil beam using the data of the displaced field "A" completes when the marker position passes 0.7, irradiation of target spots 7, 8, and 9 may continue with the first pencil beam using the data of the displaced field "B."

Likewise, if irradiation with the second pencil beam having an energy level of 95 MeV commences when the marker position is 0.0, and is midway through spot 6 when the marker position passes 0.3, then irradiation with the second pencil beam may continue with spot 7, 8 and/or 9 using the data of the displaced field "A" instead of gating the beam.

Because the energy layers are defined as part of the base field, only the displaced field layers that correspond to base-field energies can be irradiated. In the example above, target spots 1-3 would not be irradiated when the marker position passes 0.3 and target spots 1-6 would not be irradiated when the marker position passes 0.7 since they are out of the depth range.

Various embodiments of an irradiation method and methods of generating an irradiation plan are described in connection with FIGS. 2-6. It will be appreciated that more or fewer steps, actions, or processes may be incorporated into the methods without departing from the scope of the disclosure. No particular order is implied by the arrangement of blocks shown and described herein. It further will be appreciated that the methods described in conjunction with FIGS. 2-6 may be embodied in machine-executable instructions (e.g. software). The instructions can be used to cause a general-purpose or special-purpose processor that is programmed with the instructions to perform the operations described. Alternatively, the operations might be performed by specific hardware components that contain hardwired logic for performing the operations, or by any combination of programmed computer components and custom hardware components. The methods may be provided as a computer program product that may include a machine-readable medium having stored thereon instructions that may be used to program a computer (or other electronic devices) to perform the methods. For the purposes of this specification, the term "machine-readable medium" shall be taken to include any medium that is capable of storing or encoding a sequence of instructions for execution by the machine and that causes the machine to perform any one of the methodologies of the present invention. The term "machine-readable medium" shah accordingly be taken to include, but not be limited to, solid-state memories, optical and magnetic disks. Furthermore, it is common in the art to speak of software, in one form or another (e.g., program, procedure, process, application, module, logic, etc.), as taking an action or causing a result. Such expressions are merely a shorthand way of saying that execution of the software by a computer causes the processor of the computer to perform an action or produce a result.

Those skilled in the art will appreciate that various other modifications may be made within the spirit and scope of the invention. All these or other variations and modifications are contemplated by the inventors and within the scope of the invention.

What is claimed is:

1. A particle therapy system, comprising:
   a beam delivery device operable to scan a pencil beam over a target volume exhibiting phases of motion caused by a patient's physiological movement;
   a control operable to control the beam delivery device; and
   a tracking system comprising a tracking device capable of providing values in correspondence with current positions of the target volume, the tracking system being configured to measure the values and transmit analog signals continuously indicating the measured values to the control, thereby allowing the control to control the beam delivery device to continuously scan the target volume according to an irradiation plan while the target volume is in phases of motion.

2. The particle therapy system of claim 1, wherein the tracking device comprises a marker indicative of a current position of the tracking device in a correlated relationship with a current position of the target volume and an optical camera monitoring movement of the marker.

3. The particle therapy system of claim 1, wherein the tracking device is configured to measure an amount of air being inhaled and exhaled by a patient used to ascertain a volume of air currently in the lungs of the patient.

4. The particle therapy system of claim 1, wherein the beam delivery device is operable to scan a pencil beam of protons.

5. An irradiation method, comprising:
   providing an irradiation plan to a particle therapy system for irradiating a target volume exhibiting phases of motion caused by a patient's physiological movement, the particle therapy system comprising a beam delivery device operable to scan a pencil beam of particles over the target volume, the irradiation plan comprising:
   a first field for irradiating the target volume in a first phase of motion; and
   a second field for irradiating the target volume in a second phase of motion;
   monitoring a tracking device providing values in correspondence with current positions of the target volume and transmitting signals continuously indicating the values to the particle therapy system;
   applying the pencil beam of particles to the target volume according to the irradiation plan and the signals; and
   monitoring dosage delivered to the target volume.

6. The irradiation method of claim 5, wherein
   the target volume comprises a first target spot and a second target spot; and
   the first field includes data for irradiating the first and second target spots of the target volume in the first phase of motion and the second field includes data for irradiating at least the second target spot of the target volume in the second phase of motion.

7. The irradiation method of claim 6, wherein
   the applying comprises applying the pencil beam of particles to the first target spot of the target volume in the first phase of motion, and the monitoring comprises monitoring dosage delivered to the first target spot of the target volume in the first phase of motion; and
   if the monitoring of dosage delivered to the first target spot indicates that a prescribed dosage to the first target spot has been reached, and if the monitoring of the tracking device indicates that the target volume is in the first phase of motion, the method further comprises ending applying the pencil beam to the first target spot and starting applying the pencil beam to the second target spot according to data of the first field.

8. The irradiation method of claim 6, wherein
   the applying comprises applying the pencil beam of particles to the first target spot of the target volume in the first phase of motion, and the monitoring comprises monitoring dosage delivered to the first target spot of the target volume in the first phase of motion; and
   if the monitoring of dosage delivered to the first target spot indicates that a prescribed dosage to the first target spot has not been reached, and wherein if the monitoring of the tracking device indicates that the target volume is in the second phase of motion, the method further comprises determining if the second field includes data for irradiating the first target spot.

9. The irradiation method of claim 8, wherein if the determining indicates that the second field includes data for irradiating the first target spot, the method further comprises continuing to apply the pencil beam to the first target spot according to data of the second field until a prescribed dosage to the first target spot has been reached.

10. The irradiation method of claim 8, wherein if the determining indicates that the second field does not include data for irradiating the first target spot, the method further comprises applying the pencil beam to the second target spot according to data of the second field.

11. The irradiation method of claim 5, wherein the target volume consists of one or more target spots, the monitoring of motions comprises monitoring motion of each of the one or more target spots, and the providing of a signal comprises providing a signal continuously indicating a current position of each of the one or more target spots.

12. A method of generating an irradiation plan for irradiating a moving target volume with a pencil beam of particles, comprising:
- determining phases of motion of a target volume that exhibits motion in a plane generally transverse to a direction of a pencil beam of particles, the phases of motion being caused by a patient's physiological movement;
- defining a first field for scanning the target volume with the pencil beam of particles when the target volume is in a first phase of motion;
- defining a second field for scanning the target volume with the pencil beam of particles when the target volume is in a second phase of motion;
- generating an irradiation plan for continuously irradiating the target volume moving from the first phase to the second phase, wherein while the target volume is in the first phase of motion the first field is used for the pencil beam to scan the target volume and wherein while the target volume is in the second phase of motion the second field is used for the pencil beam to scan the target volume.

13. The method of claim 12, wherein the target volume comprises one or more target spots, and wherein the defining of the first field comprises providing data on positions of each of the one or more target spots, and the defining of the second field comprises providing data on positions of each of the one or more target spots.

14. The method of claim 13, wherein at least one of the one or more target spots is continuously irradiated with the pencil beam while the target volume moves from the first phase to the second phase of motion to reach a prescribed dosage, wherein in the first phase of motion, the at least one of the one or more target spots is irradiated according to the first field and in the second phase of motion, the at least one of the one or more target spots is irradiated according to the second field.

15. The method of claim 13, wherein the determining of phases of motion of the target volume comprises determining of phases of motion of each of the one or more target spots.

16. The method of claim 12, wherein the pencil beam of particles comprises protons.

17. A method of generating an irradiation plan for a moving target volume with pencil beams of particles, comprising:
- determining phases of motion of a target volume that exhibits motion in a dimension generally parallel to a direction of a pencil beam of particles, the phases of motion being caused by a patient's physiological movement, wherein the target volume comprises at least a first layer and a second layer along the direction of the pencil beam of particles;
- defining a first field for irradiating the target volume in a first phase of motion, wherein at least a first pencil beam having a first energy level scans the first layer of the target volume and a second pencil beam having a second energy level scans the second layer of the target volume;
- defining a second field for irradiating the target volume in a second phase of motion, wherein the first pencil beam having the first energy level scans the second layer of the target volume or the second pencil beam having the second energy level scans the first layer of the target volume;
- generating an irradiation plan for continuously irradiating the target volume when moving from the first phase to the second phase, wherein the first pencil beam having the first energy level continuously scans the target volume when moving from the first phase to the second phase, or the second pencil beam having the second energy level continuously scans the target volume when moving from the first phase to the second phase.

18. The method of claim 17, wherein the defining of the first field comprises providing data on locations of the first and second layers of the target volume, and the defining of the second field comprises providing data on locations of the first and second layers of the target volume.

19. The method of claim 17, wherein the first pencil beam having the first energy level continuously irradiates the target volume when the target volume moves from the first phase to the second phase, wherein the first pencil beam having the first energy level irradiates the first layer of the target volume according to the first field when the target volume is in the first phase and irradiates the second layer of the target volume according to the second field when the target volume is in the second phase; or
- the second pencil beam having the second energy level continuously irradiates the target volume while moving from the first phase to the second phase of motions, wherein the second pencil beam having the second energy irradiates the second layer of the target volume according to the first field when the target volume is in the first phase and irradiates the first layer of the target volume according to the second field when the target volume in the second phase.

20. The method of claim 17, wherein the determining of phases of motion of the target volume comprises determining of phases of motion of each of the first and second layers of the target volume.

21. The method of claim 17, wherein the pencil beam of particles comprises protons.

* * * * *

UNITED STATES PATENT AND TRADEMARK OFFICE
CERTIFICATE OF CORRECTION

PATENT NO.         : 10,293,185 B2
APPLICATION NO.    : 15/474856
DATED              : May 21, 2019
INVENTOR(S)        : J. Janssen Page 1 of 1

It is certified that error appears in the above-identified patent and that said Letters Patent is hereby corrected as shown below:

In the Specification

At Column 13 Line 22, please replace "shah" with -shall-.

Signed and Sealed this
Sixteenth Day of July, 2019

Andrei Iancu
*Director of the United States Patent and Trademark Office*